United States Patent [19]

Teach

[11] 3,959,304

[45] May 25, 1976

[54] CERTAIN 3-HALOACYL-2,2,5-TRIMETHYL-OXAZOLIDINES

[75] Inventor: Eugene G. Teach, El Cerrito, Calif.

[73] Assignee: Stauffer Chemical Company, Westport, Conn.

[22] Filed: Apr. 7, 1975

[21] Appl. No.: 566,019

Related U.S. Application Data

[63] Continuation-in-part of Ser. No. 484,514, July 1, 1974, abandoned, which is a continuation of Ser. No. 356,548, May 2, 1973, abandoned, which is a continuation-in-part of Ser. No. 297,582, Oct. 13, 1972, abandoned.

[52] U.S. Cl. .............................. 260/307 FA; 71/88; 71/90
[51] Int. Cl.² ........................................ C07D 263/04
[58] Field of Search ............................. 260/307 FA

[56] References Cited
UNITED STATES PATENTS 3,707,541  12/1972  Lajiness .............................. 260/307

*Primary Examiner*—Richard J. Gallagher
*Attorney, Agent, or Firm*—Harry A. Pacini

[57] ABSTRACT

Substituted oxazolidines and thiazolidines having the formula

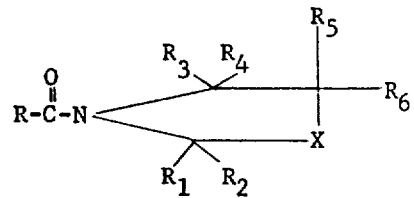

in which X is oxygen or sulfur; R is haloalkyl, alkyl or alkylthio; and $R_1$, $R_2$, $R_3$, $R_4$, $R_5$ and $R_6$ are independently selected from the group consisting of hydrogen, lower alkyl, alkoxyalkyl and lower alkylol; provided that when X is oxygen and R is alkyl, then at least one of $R_1$, $R_2$, $R_3$, $R_4$, $R_5$ and $R_6$ is other than hydrogen. The compounds are active as an antidote against crop injury, when used with various herbicides.

13 Claims, No Drawings

CERTAIN 3-HALOACYL-2,2,5-TRIMETHYL-OXAZOLIDINES

This application is a continuation-in-part of copending application Ser. No. 484,514, filed July 1, 1974 now abandoned, which in turn is a continuation of then copending application Ser. No. 356,548, filed May 2, 1973, now abandoned, which in turn is a continuation-in-part of then copending application Ser. No. 297,582, filed Oct. 13, 1972, now abandoned.

This invention relates to certain novel substituted oxazolidines and thiazolidines which are useful as antidotes against crop injury by various herbicides. The compounds of the present invention are new compositions of matter and correspond to the general formula

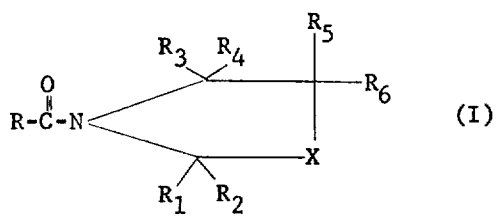
(I)

in which X is oxygen or sulfur; R is haloalkyl, alkyl or alkylthio; and $R_1$, $R_2$, $R_3$, $R_4$, $R_5$ and $R_6$ are independently selected from the group consisting of hydrogen, lower alkyl, alkoxyalkyl and lower alkylol; provided that when X is oxygen and R is alkyl, then at least one of $R_1$, $R_2$, $R_3$, $R_4$, $R_5$ or $R_6$ is other than hydrogen.

In the above description, the following embodiments are intended for the various substituent groups: For R, haloalkyl and alkyl preferably includes, unless otherwise provided for, those members which contain from 1 to 10 carbon atoms, inclusive, in both straight chain and branched chain configurations, and the term halo includes chloro and bromo as mono, di, tri, tetra and per substitutions. As exemplary of the alkyl portion within the preferred embodiment are the following: Methyl, ethyl, n-propyl, isopropyl, n-butyl, sec.-butyl, 1,1-dimethylbutyl, amyl, isoamyl, 2,4,4-trimethylpentyl, n-hexyl, isohexyl, n-heptyl, n-octyl, isooctyl, nonyl, and decyl. The term alkylthio preferably includes those members which contain from 1 to 4 carbon atoms, inclusive, for example, methylthio, ethylthio, n-propylthio, isopropylthio, n-butylthio, t-butylthio, and the like. For $R_1$, $R_2$, $R_3$, $R_4$, $R_5$ and $R_6$, the term lower alkyl preferably includes, unless otherwise provided for, those members which contain from 1 to 4 carbon atoms, inclusive, for example, methyl, ethyl, n-propyl, isopropyl, n-butyl, sec.-butyl, tert.-butyl, and the like. The term alkoxyalkyl preferably includes those members having a total of 2 to 4 carbon atoms, inclusive, for example, methoxymethyl, methoxyethyl, ethoxyethyl, ethoxymethyl and the like. The term lower alkylol preferably includes those members having 1 to 4 carbon atoms, inclusive, for example, methylol, ethylol, propylol and butylol.

PREFERRED EMBODIMENTS OF THE INVENTION

The preferred embodiments of the invention are realized when the following substitutions are present in compounds corresponding to the general formula (I), supra.

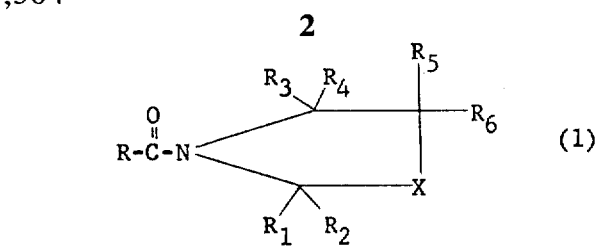
(1)

in which X is oxygen, R is selected from the group dichloromethyl, tribromomethyl, trichloromethyl, 1-bromoethyl, monobromomethyl, 1,2,4,4-tetrabromopentyl, 2-chloroethyl, 1,2-dibromoethyl, 2-bromoethyl, ω-bromodecyl, 3-chloropropyl, 2-chloropropyl, 1-bromopropyl, 1-bromobutyl, 5-bromopentyl; $R_1$ is methyl, $R_2$ is selected from the group methyl, ethyl, t-butyl, i-propyl; $R_3$, $R_4$, $R_5$ and $R_6$ are each hydrogen; provided that when R is dichloromethyl, $R_2$ is other than methyl;

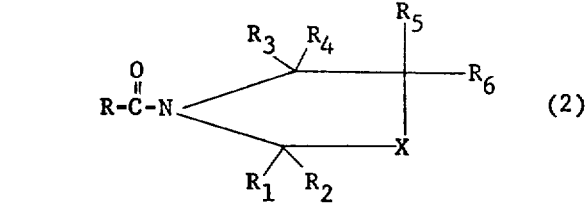
(2)

in which X is oxygen, R is monochloromethyl, $R_2$ is selected from the group methyl, ethyl, t-butyl, i-propyl; and $R_3$, $R_4$, $R_5$ and $R_6$ are each hydrogen;

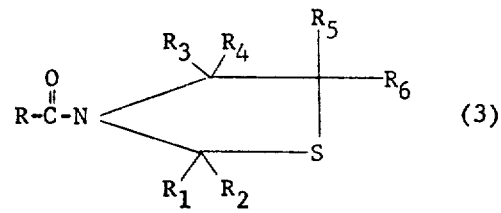
(3)

in which R is haloalkyl having 1 to 10 carbon atoms, inclusive, and halo is selected from chloro and bromo, $R_1$ is lower alkyl having from 1 to 4 carbon atoms, inclusive, $R_2$ is lower alkyl having from 1 to 4 carbon atoms, inclusive, and $R_3$, $R_4$, $R_5$ and $R_6$ are each hydrogen;

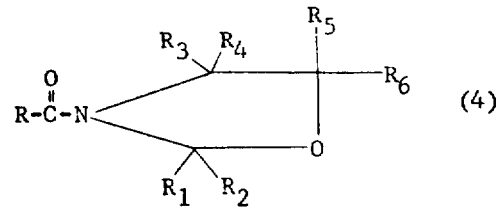
(4)

in which R is selected from the group tribromomethyl, monochloromethyl, dichloromethyl, 1-bromoethyl, monobromomethyl, 1,2-dibromoethyl, 2-chloropropyl, 1-bromopropyl, 1-bromobutyl, 3-chloropropyl, 5-bromopentyl; $R_1$ is methyl, $R_2$ is methyl, $R_5$ is methyl and $R_3$, $R_4$ and $R_6$ are each hydrogen;

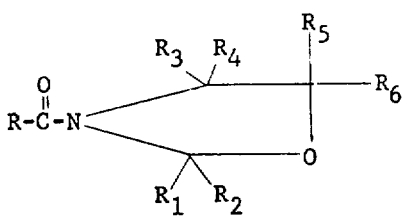

in which R is selected from the group consisting of dichloromethyl, trichloromethyl, monobromomethyl, 1-bromoethyl and tribromomethyl, $R_1$ is methyl, $R_2$ is methyl, $R_3$ is methyl and $R_4$ is methyl, and $R_5$ and $R_6$ are each hydrogen;

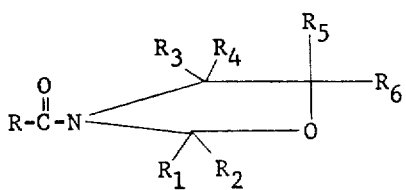

in which R is haloalkyl having 1 to 10 carbon atoms, inclusive, halo is selected from chloro and bromo, $R_1$ is lower alkyl having 1 to 4 carbon atoms, inclusive, $R_5$ is lower alkyl having from 1 to 4 carbon atoms, inclusive, and $R_2$, $R_3$, $R_4$ and $R_6$ are each hydrogen;

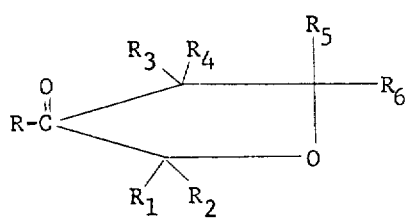

in which R is haloalkyl having from 1 to 10 carbon atoms, inclusive, halo is selected from chloro and bromo, $R_3$ is lower alkyl having from 1 to 4 carbon atoms, inclusive, and $R_1$, $R_2$, $R_4$, $R_5$ and $R_6$ are each hydrogen.

(8) Also, N-haloacyl (2-alkylated) oxazolidine wherein the haloacyl group is $C_{2-4}$ acyl, and the 4 and 5 carbon atoms of the oxazolidine ring are satisfied by hydrogen or $C_{1-6}$ alkyl groups.

Some of the compounds of this invention are active herbicides and can be used in herbicidal compositions to control the growth of undesirable vegetation. The compounds also are useful in plant growth regulating compositions, nematocidal, algicidal, bacteriostatic and fungicidal compositions.

Among the many herbicidal compounds commercially available, the thiocarbamates, alone or admixed with other herbicides such as the triazines, have reached a relatively high degree of commercial success. These herbicides are immediately toxic to a large number of weed pests at different concentrations varying with the resistance of the weed pests. Some examples of these compounds are described and claimed in the U.S. Pat. Nos. 2,913,327, 3,037,853, 3,175,897, 3,185,720, 3,198,786 and 3,582,314.

It has been found in practice that the use of these thiocarbamates as herbicides on crops sometimes causes serious injuries to the crop plants. When used in the recommended amounts in the soil to control many broadleaf weeds and grasses, serious malformation and stunting of the crop plants result. This abnormal growth in the crop plants results in loss of crop yield. Previous attempts to overcome this problem involves the treatment of the crop seed with certain antagonistic agents prior to planting, see U.S. Pat. Nos. 3,131,509 and 3,564,768. These antagonistic agents have not been notably successful. The aforementioned patent specifically exemplifies the treatment of seeds employing compounds of a different chemical class not suggestive of the present invention.

Other herbicidal compounds whose effect can be modified by the instant compounds include the acetanilides, such as 2-chloro-2',6'-diethyl-N-(methoxymethyl)acetanilide and the urea-type herbicides, such as 3-(3,4-dichlorophenyl)-1,1-dimethylurea.

It has been discovered that plants can be protected against injury by thiocarbamate-type herbicides, alone or mixed with other herbicides. An alternative mode of action is for the tolerance of the plants to the active herbicidal compounds to be substantially increased by adding to the soil an antidotally effective amount of a compound described in this invention according to the formula

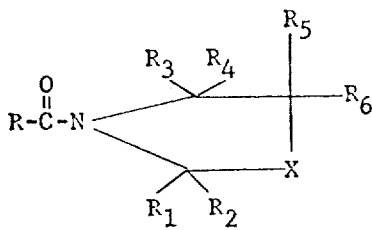

in which X, R, $R_1$, $R_2$, $R_3$, $R_4$, $R_5$ and $R_6$ are as defined above.

As an alternative mode of action, the compounds of this invention may interfere with the normal herbicidal action of the thiocarbamate herbicides to render them selective in their action.

Whichever mode of action is operative, the corresponding beneficial and desirable effect is the continued herbicidal effect of the thiocarbamate with the accompanying decreased herbicidal effect on desired crop species. This advantage and utility will become more apparent hereinafter.

Therefore, the terms herbicide, antidote or antidotal amount, is meant to describe that effect which tends to counteract the normal injurious herbicidal response that the herbicide might otherwise produce. Whether it is to be termed a remedy, interferant, protectant, or the like, will depend upon the exact mode of action. The mode of action is varied, but the effect, which is desirable, is the result of the method of treating the soil in which a crop is planted. Hitherto, there have been no systems which have been satisfactory for this purpose.

The compounds of this invention represented by the above formula can be prepared by several different procedures depending upon the starting materials.

The oxazolidine and thiazolidine intermediates are prepared by the condensation of an amino alcohol or mercaptan with a suitable aldehyde or ketone in boiling benzene with the continuous separation of water. This method is described by Bergmann et al., JACS 75 358 (1953). Usually, the oxazolidines and thiazolidines intermediates are pure enough to be used directly without further purification. Aliquots of these solutions are then used to prepare the compounds of this invention.

The appropriate intermediate is reacted with an acid chloride in the presence of a hydrogen chloride acceptor, such as triethylamine, to prepare the desired compound. Workup and purification procedures involve standard methods of extraction, distillation or crystallization.

The compounds of the present invention and their preparation are more particularly illustrated by the following examples. Following the examples of preparation is a table of compounds which are prepared according to the procedures described herein. Compound numbers have been assigned to them and are used for identification throughout the balance of the specification.

EXAMPLE I

Preparation of 2,2-dimethyl-3-dichloroacetyl oxazolidine.

Five and one-tenth grams of 2,2-dimethyl oxazolidine dissolved in 50 ml. of benzene was treated with 5.5 g. of triethylamine and 7.4 g. of dichloroacetyl chloride was added dropwise with stirring and cooling in an ice bath. The mixture was poured into water, the benzene solution separated, dried over anhydrous magnesium sulfate and the solvent stripped under vacuum. The product was a waxy solid which had a melting point of 113°–115°C. on recrystallization from diethyl ether.

EXAMPLE II

Preparation of 2,2,5-trimethyl-3-dichloroacetyl oxazolidine.

Eighteen milliliters of a benzene solution containing 4.6 g. of 2,2,5-trimethyl oxazolidine was added to 25 ml. of benzene and 4.5 g. of triethylamine. Five and nine-tenths grams of dichloroacetyl chloride was added dropwise with stirring and cooling in an ice bath. When reaction was complete the mixture was poured into water and the benzene layer separated, dried over anhydrous magnesium sulfate and the benzene removed under vacuum. Yield was 7.7 g. of an oil, $n_D^{30} = 1.4950$.

EXAMPLE III

Preparation of 2,2-dimethyl-3-dichloroacetyl thiazolidine.

Four and seven-tenths grams of 2,2-dimethyl thiazolidine and 4.5 g. of triethylamine were dissolved in 50 ml. of methylene chloride and 5.9 g. of dichloroacetyl chloride was added dropwise with stirring. The mixture was cooled in a water bath at room temperature. When reaction was complete, the mixture was poured into water and the solvent layer separated, dried over anhydrous magnesium sulfate, and the solvent removed under vacuum. Yield was 3.6 g. of a waxy solid. Recrystallization of another sample from diethyl ether gave a white solid, m.p. 109°–111°C.

EXAMPLE IV

Preparation of 2,2,5-trimethyl-3(2',3'-dibromopropionyl)oxazolidine.

Fourteen milliliters of a benzene solution containing 3.5 g. of 2,2,5-trimethyl oxazolidine was added to 25 ml. of benzene and 3.5 g. of triethylamine. Seven and one-half grams of 2,3-dibromopropionyl chloride was added dropwise with stirring and cooling in an ice bath. When reaction was complete, the mixture was poured into water and the benzene layer separated, dried over anhydrous magnesium sulfate and the solvent stripped under vacuum. The yield was 5.7 g. of an oil, $n_D^{30} = 1.5060$.

EXAMPLE V

Preparation of 2,2-dimethyl-3-dibromoacetyl thiazolidine.

To a mixture of 3.5 g. of 2,2-dimethyl thiazolidine, 50 ml. of benzene and 7.1 g. of dibromoacetyl chloride mixed in an ice bath was added 3.1 g. of triethylamine dropwise with stirring and continued cooling. When reaction was complete, the mixture was poured into water and the benzene layer separated, dried over magnesium sulfate and the benzene removed under vacuum. Yield was 8.5 g. of a dark oil.

EXAMPLE VI

Preparation of 2-ethyl-3-S-ethylthiocarbonyl oxazolidine.

Sixteen and one-half milliliters of a benzene solution of 2-ethyl oxazolidine was added to 50 ml. of benzene and 4.1 g. of triethylamine. Five grams of ethyl chlorothiolformate was added dropwise with stirring and cooling in an ice bath. The mixture was poured into water and the benzene solution separated, dried over anhydrous magnesium sulfate and the benzene stripped under vacuum. Yield was 5.6 g. of an oil, $n_D^{30} = 1.5130$.

EXAMPLE VII

Preparation of 2,2-dimethyl-3-heptanoyl oxazolidine.

Sixteen and one-half milliliters of a benzene solution containing 4.6 g. of 2,2-dimethyl oxazolidine was added to 50 ml. of benzene and 4.1 g. of triethylamine. To this mixture 6 g. of n-heptanoyl chloride was added dropwise with stirring and cooling in an ice bath. The mixture was poured into water and the benzene layer extracted, dried over magnesium sulfate and the benzene removed under vacuum. Yield was 7.5 g. of an oil, $n_D^{30} = 1.4598$.

TABLE I

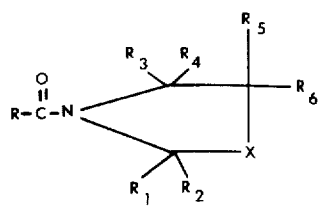

| COMPOUND NUMBER | R | $R_1$ | $R_2$ | $R_3$ | $R_4$ | $R_5$ | $R_6$ | X | m.p. °C. or $n_D^{30}$ |
|---|---|---|---|---|---|---|---|---|---|
| 1 | CHCl$_2$ | CH$_3$ | CH$_3$ | H | H | H | H | O | 116–118 |
| 2 | CH$_2$Cl | CH$_3$ | CH$_3$ | H | H | H | H | O | 1.4932 |
| 3 | CBr$_3$ | CH$_3$ | CH$_3$ | H | H | H | H | O | 1.5560 |
| 4 | CBr$_3$ | CH$_3$ | CH$_3$ | H | H | CH$_3$ | H | O | Glass |
| 5 | CH$_2$Cl | CH$_3$ | CH$_3$ | H | H | CH$_3$ | H | O | 1.4842 |
| 6 | CHCl$_2$ | CH$_3$ | CH$_3$ | H | H | CH$_3$ | H | O | 1.4950 |
| 7 | CH$_2$Cl | CH$_3$ | CH$_3$ | C$_2$H$_5$ | H | H | H | O | 1.4900 |
| 8 | CHCl$_2$ | CH$_3$ | CH$_3$ | C$_2$H$_5$ | H | H | H | O | 1.4950 |
| 9 | CCl$_3$ | CH$_3$ | CH$_3$ | C$_2$H$_5$ | H | H | H | O | 1.4970 |
| 10 | CBr$_3$ | CH$_3$ | CH$_3$ | C$_2$H$_5$ | H | H | H | O | 1.5428 |
| 11 | CH$_3$CHBr | CH$_3$ | CH$_3$ | H | H | CH$_3$ | H | O | 1.4993 |
| 12 | CH$_3$CHBr | CH$_3$ | CH$_3$ | C$_2$H$_5$ | H | H | H | O | 1.4993 |
| 13 | CH$_2$Cl | CH$_3$ | C$_2$H$_5$ | H | H | H | H | O | 1.4928 |
| 14 | CHCl$_2$ | CH$_3$ | C$_2$H$_5$ | H | H | H | H | O | 1.4982 |
| 15 | CCl$_3$ | CH$_3$ | C$_2$H$_5$ | H | H | H | H | O | 1.5034 |
| 16 | CH$_3$CHBr | CH$_3$ | C$_2$H$_5$ | H | H | H | H | O | 1.5058 |
| 17 | CBr$_3$ | CH$_3$ | C$_2$H$_5$ | H | H | H | H | O | 95–97 |
| 18 | CH$_2$Br | CH$_3$ | C$_2$H$_5$ | H | H | H | H | O | 1.5097 |
| 19 | CH$_2$Br | CH$_3$ | CH$_3$ | H | H | CH$_3$ | H | O | 1.5020 |
| 20 | CH$_2$Br | CH$_3$ | CH$_3$ | C$_2$H$_5$ | H | H | H | O | 1.5048 |
| 21 | CH$_3$(CHBr)$_4$ | CH$_3$ | CH$_3$ | H | H | H | H | O | 1.5658 |
| 22 | CH$_2$Cl | CH$_3$ | CH$_3$ | CH$_3$ | CH$_3$ | H | H | O | 1.4843 |
| 23 | CHCl$_2$ | CH$_3$ | CH$_3$ | CH$_3$ | CH$_3$ | H | H | O | 120–123 |
| 24 | CCl$_3$ | CH$_3$ | CH$_3$ | CH$_3$ | CH$_3$ | H | H | O | 1.5031 |
| 25 | CH$_2$Br | CH$_3$ | CH$_3$ | CH$_3$ | CH$_3$ | H | H | O | 1.5116 |
| 26 | CH$_3$CHBr | CH$_3$ | CH$_3$ | CH$_3$ | CH$_3$ | H | H | O | 1.5140 |
| 27 | CBr$_3$ | CH$_3$ | CH$_3$ | CH$_3$ | CH$_3$ | H | H | O | 1.5610 |
| 28 | ClCH$_2$CH$_2$ | CH$_3$ | CH$_3$ | H | H | H | H | O | 1.4538 |
| 29 | CHCl$_2$ | C$_2$H$_5$ | H | H | H | H | H | S | 1.5458 |
| 30 | CHCl$_2$ | CH$_3$ | CH$_3$ | H | H | H | H | S | 109–111 |
| 31 | CH$_2$BrCHBr | CH$_3$ | C$_2$H$_5$ | H | H | H | H | O | 1.5170 |
| 32 | CH$_2$BrCHBr | CH$_3$ | CH$_3$ | H | H | CH$_3$ | H | O | 1.5060 |
| 33 | CH$_2$BrCHBr | CH$_3$ | CH$_3$ | C$_2$H$_5$ | H | H | H | O | 1.5083 |
| 34 | CH$_2$BrCHBr | CH$_3$ | CH$_3$ | H | H | H | H | O | 1.5178 |
| 35 | CH$_2$BrCHBr | CH$_3$ | t-C$_4$H$_9$ | H | H | H | H | O | 1.5165 |
| 36 | CHCl$_2$ | CH$_3$ | t-C$_4$H$_9$ | H | H | H | H | O | 1.4949 |
| 37 | CBr$_3$ | CH$_3$ | t-C$_4$H$_9$ | H | H | H | H | O | 1.5431 |
| 38 | CHCl$_2$ | H | CH$_3$OCH$_2$ | H | CH$_3$ | CH$_3$ | H | O | 1.5033 |
| 39 | CHCl$_2$ | CH$_3$OCH$_2$ | H | H | H | H | H | O | 1.5132 |
| 40 | CHCl$_2$ | C$_3$H$_7$ | H | H | H | H | H | O | 1.4988 |
| 41 | CHCl$_2$ | C$_2$H$_5$ | H | H | H | H | H | O | 1.5126 |
| 42 | CHBr$_2$ | C$_2$H$_5$ | H | H | H | H | H | O | 1.5750 |
| 43 | CBr$_3$ | C$_2$H$_5$ | H | H | H | H | H | O | 1.5610 |
| 44 | CH$_2$Br | C$_2$H$_5$ | H | H | H | H | H | O | 1.5200 |
| 45 | CH$_3$CHBr | C$_2$H$_5$ | H | H | H | H | H | O | 1.5140 |
| 46 | (CH$_3$)$_2$CBr | C$_2$H$_5$ | H | H | H | H | H | O | 1.4958 |
| 47 | CH$_2$BrCHBr | C$_2$H$_5$ | H | H | H | H | H | O | 1.5273 |
| 48 | CH$_2$Cl | C$_2$H$_5$ | H | H | H | H | H | O | 1.5020 |
| 49 | CHCl$_2$ | C$_2$H$_5$ | H | H | H | CH$_3$ | H | O | 1.4955 |
| 50 | CH$_2$Cl | C$_2$H$_5$ | H | H | H | CH$_3$ | H | O | 1.4890 |
| 51 | CH$_2$Br | C$_2$H$_5$ | H | H | H | CH$_3$ | H | O | 1.5064 |
| 52 | CHBr$_2$ | C$_2$H$_5$ | H | H | H | CH$_3$ | H | O | Glass |
| 53 | CBr$_3$ | C$_2$H$_5$ | H | H | H | CH$_3$ | H | O | Glass |
| 54 | CH$_3$CHBr | C$_2$H$_5$ | H | H | H | CH$_3$ | H | O | 1.4978 |
| 55 | CH$_2$BrCHBr | C$_2$H$_5$ | H | H | H | CH$_3$ | H | O | 1.5138 |
| 56 | (CH$_3$)$_2$CBr | C$_2$H$_5$ | H | H | H | CH$_3$ | H | O | 1.4851 |
| 57 | CHCl$_2$ | H | H | C$_2$H$_5$ | H | H | H | O | 1.5030 |
| 58 | CHBr$_2$ | H | H | C$_2$H$_5$ | H | H | H | O | Dark liquid |
| 59 | CBr$_3$ | H | H | C$_2$H$_5$ | H | H | H | O | 1.5531 |
| 60 | CH$_2$Br | H | H | C$_2$H$_5$ | H | H | H | O | 1.5173 |
| 61 | CH$_3$CHBr | H | H | C$_2$H$_5$ | H | H | H | O | 1.5076 |
| 62 | (CH$_3$)$_2$CBr | H | H | C$_2$H$_5$ | H | H | H | O | 1.4852 |
| 63 | CH$_2$BrCHBr | H | H | C$_2$H$_5$ | H | H | H | O | 1.5249 |
| 64 | CCl$_3$ | H | H | C$_2$H$_5$ | H | H | H | O | 1.5048 |
| 65 | CH$_2$Cl | H | H | C$_2$H$_5$ | H | H | H | O | 1.4998 |
| 66 | CHCl$_2$ | CH$_3$ | H | H | H | H | H | O | 1.5112 |
| 67 | CCl$_3$ | CH$_3$ | H | H | H | H | H | O | 1.5148 |
| 68 | CH$_2$Cl | CH$_3$ | H | H | H | H | H | O | 1.5077 |
| 69 | CH$_2$Br | CH$_3$ | H | H | H | H | H | O | 1.5263 |
| 70 | CHBr$_2$ | CH$_3$ | H | H | H | H | H | O | 1.5471 |
| 71 | CBr$_3$ | CH$_3$ | H | H | H | H | H | O | Dark liquid |
| 72 | CH$_2$BrCHBr | CH$_3$ | H | H | H | H | H | O | 1.5280 |
| 73 | CH$_3$CHBr | CH$_3$ | H | H | H | H | H | O | 1.5162 |
| 74 | (CH$_3$)$_2$CBr | CH$_3$ | H | H | H | H | H | O | 1.5013 |

TABLE I-continued

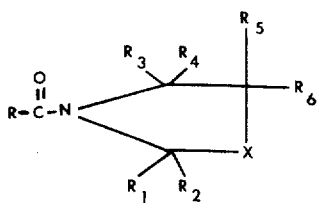

| COMPOUND NUMBER | R | $R_1$ | $R_2$ | $R_3$ | $R_4$ | $R_5$ | $R_6$ | X | m.p. °C. or $n_D^{30}$ |
|---|---|---|---|---|---|---|---|---|---|
| 75 | $CHCl_2$ | $CH_3$ | H | H | H | $CH_3$ | H | O | 1.4983 |
| 76 | $CCl_3$ | $CH_3$ | H | H | H | $CH_3$ | H | O | 1.4990 |
| 77 | $CH_2Cl$ | $CH_3$ | H | H | H | $CH_3$ | H | O | 1.4958 |
| 78 | $CHBr_2$ | $CH_3$ | H | H | H | $CH_3$ | H | O | Dark liquid |
| 79 | $CH_3CHBr$ | $CH_3$ | H | H | H | $CH_3$ | H | O | 1.5083 |
| 80 | $CHBr_2$ | $C_2H_5$ | H | H | H | H | H | S | 1.5782 |
| 81 | $CH_2BrCHBr$ | $C_2H_5$ | H | H | H | H | H | S | 1.5650 |
| 82 | $CCl_3$ | $CH_3$ | $CH_3$ | H | H | H | H | S | 1.5638 |
| 83 | $CHBr_2$ | $CH_3$ | $CH_3$ | H | H | H | H | S | Dark liquid |
| 84 | $CH_3CHBr$ | $CH_3$ | $CH_3$ | H | H | H | H | S | 1.5520 |
| 85 | $CHCl_2$ | H | H | H | H | H | H | S | 75–77 |
| 86 | $CHCl_2$ | $CH_3$ | $i$-$C_3H_7$ | H | H | H | H | O | 1.4960 |
| 87 | $CHCl_2$ | $CH_3$ | $CH_3$ | $CH_3$ | $CH_2OH$ | H | H | O | 1.4960 |
| 88 | $CH_2BrC(CH_3)Br$ | $C_2H_5$ | H | H | H | H | H | O | 1.5318 |
| 89 | $CH_2BrC(CH_3)Br$ | $C_2H_5$ | H | H | H | $CH_3$ | H | O | 1.5225 |
| 90 | $CH_2BrC(CH_3)Br$ | $CH_3$ | H | H | H | $CH_3$ | H | O | 1.5210 |
| 91 | $CHCl_2$ | $C_2H_5$ | H | $C_2H_5$ | H | H | H | O | 1.4947 |
| 92 | $C_2H_5S$ | H | H | $C_2H_5$ | H | H | H | O | 1.4998 |
| 93 | $C_2H_5S$ | $CH_3$ | H | H | H | $CH_3$ | H | O | 1.4965 |
| 94 | $C_2H_5S$ | $C_2H_5$ | H | H | H | $CH_3$ | H | O | 1.4973 |
| 95 | $C_2H_5S$ | $C_2H_5$ | H | $C_2H_5$ | H | H | H | O | 1.4928 |
| 96 | $CCl_3$ | $C_2H_5$ | H | $C_2H_5$ | H | H | H | O | 1.4937 |
| 97 | $CH_2BrCHBr$ | $C_2H_5$ | H | $C_2H_5$ | H | H | H | O | 1.5198 |
| 98 | $CH_2BrC(CH_3)Br$ | $C_2H_5$ | H | $C_2H_5$ | H | H | H | O | 1.5202 |
| 99 | $CH_2BrCH_2$ | $C_2H_5$ | H | $C_2H_5$ | H | H | H | O | 1.4920 |
| 100 | $CHCl_2$ | $CH_3$ | H | $C_2H_5$ | H | H | H | O | 1.4960 |
| 101 | $C_3H_7S$ | $CH_3$ | H | $C_2H_5$ | H | H | H | O | 1.4900 |
| 102 | $i$-$C_3H_7S$ | $CH_3$ | H | $C_2H_5$ | H | H | H | O | 1.4875 |
| 103 | $CCl_3$ | $CH_3$ | H | $C_2H_5$ | H | H | H | O | 1.4990 |
| 104 | $CH_2Br$ | $CH_3$ | H | $C_2H_5$ | H | H | H | O | 1.5070 |
| 105 | $CH_2BrCHBr$ | $CH_3$ | H | $C_2H_5$ | H | H | H | O | 1.5168 |
| 106 | $CH_2BrC(CH_3)Br$ | $CH_3$ | H | $C_2H_5$ | H | H | H | O | 1.5160 |
| 107 | $CH_2BrCH_2$ | $CH_3$ | H | $C_2H_5$ | H | H | H | O | 1.4950 |
| 108 | $C_4H_9S$ | $CH_3$ | H | $C_2H_5$ | H | H | H | O | 1.4928 |
| 109 | $C_4H_9S$ | $C_2H_5$ | H | $C_2H_5$ | H | H | H | O | 1.4880 |
| 110 | $CH_3S$ | $CH_3$ | H | $C_2H_5$ | H | H | H | O | 1.4980 |
| 111 | $C_6H_{13}$ | $CH_3$ | $CH_3$ | H | H | H | H | O | 1.4598 |
| 112 | $CH_3S$ | $CH_3$ | $CH_3$ | $C_2H_5$ | H | H | H | O | 1.4913 |
| 113 | $n$-$C_3H_7S$ | $CH_3$ | $CH_3$ | $C_2H_5$ | H | H | H | O | 1.4858 |
| 114 | $i$-$C_3H_7S$ | $CH_3$ | $CH_3$ | $C_2H_5$ | H | H | H | O | 1.4828 |
| 115 | $CH_2BrCH_2$ | $CH_3$ | $CH_3$ | H | H | H | H | O | 1.4912 |
| 116 | $CH_2BrCHBr$ | H | H | $CH_3$ | $CH_3$ | H | H | O | 1.5221 |
| 117 | $CH_2BrCH_2$ | $CH_3$ | $CH_3$ | H | H | H | H | S | 1.5263 |
| 118 | $CH_2BrCHBr$ | $CH_3$ | $CH_3$ | H | H | H | H | S | 1.5573 |
| 119 | $CH_2BrCH_2$ | H | H | $CH_3$ | $CH_3$ | H | H | O | 1.4890 |
| 120 | $CH_2Br$ | H | H | H | H | H | H | S | 1.6032 |
| 121 | $CH_3CHBr$ | H | H | H | H | H | H | S | 1.5720 |
| 122 | $CH_2BrCH_2$ | H | H | H | H | H | H | S | 1.5629 |
| 123 | $CH_2BrCHBr$ | H | H | H | H | H | H | S | 1.5742 |
| 124 | $CH_3C(CH_3)Br$ | H | H | H | H | H | H | S | 1.5420 |
| 125 | $CH_2ClCH_2$ | H | H | H | H | H | H | S | 1.5475 |
| 126 | $BrCH_2(CH_2)_nCH_2$ | $CH_3$ | $CH_3$ | H | H | H | H | O | 1.4898 |
| 127 | $ClCH_2CH_2CH_2$ | $CH_3$ | $CH_3$ | H | H | H | H | O | 1.4880 |
| 128 | $ClCH_2CH_2CH_2$ | $CH_3$ | $CH_3$ | H | H | H | H | S | 1.5183 |
| 129 | $CH_3CHClCH_2$ | $CH_3$ | $CH_3$ | H | H | H | H | O | 1.4896 |
| 130 | $CH_3CHClCH_2$ | $CH_3$ | $CH_3$ | H | H | H | H | O | 1.5115 |
| 131 | $CH_3CHClCH_2$ | $CH_3$ | $CH_3$ | H | H | $CH_3$ | H | O | 1.4701 |
| 132 | $C_2H_5CHBr$ | $CH_3$ | $CH_3$ | H | H | H | H | O | 1.5020 |
| 133 | $C_2H_5CHBr$ | $CH_3$ | $CH_3$ | H | H | H | H | S | 1.5288 |
| 134 | $C_2H_5CHBr$ | $CH_3$ | $CH_3$ | H | H | $CH_3$ | H | O | 1.4900 |
| 135 | $C_3H_7CHBr$ | $CH_3$ | $CH_3$ | H | H | H | H | O | 1.4972 |
| 136 | $C_3H_7CHBr$ | $CH_3$ | $CH_3$ | H | H | H | H | S | 1.5220 |
| 137 | $C_3H_7CHBr$ | $CH_3$ | $CH_3$ | H | H | $CH_3$ | H | O | 1.4870 |
| 138 | $CH_2ClCH_2CH_2$ | $CH_3$ | $CH_3$ | H | H | $CH_3$ | H | O | 1.4747 |
| 139 | $CH_2Br(CH_2)_4$ | $CH_3$ | $CH_3$ | H | H | H | H | O | 1.4970 |
| 140 | $CH_2Br(CH_2)_4$ | $CH_3$ | $CH_3$ | H | H | $CH_3$ | H | O | 1.4886 |
| 141 | $CH_2Br(CH_2)_4$ | $CH_3$ | $CH_3$ | H | H | H | H | S | 1.5249 |
| 142 | $CH_2BrCBr(CH_3)$ | H | H | H | H | H | H | S | Semi-solid |
| 143 | $CH_2Cl$ | H | H | H | H | H | H | S | 1.5540 |
| 144 | $CHCl_2$ | $CH_3$ | H | $C_2H_5$ | H | H | H | S | 1.5443 |
| 145 | $CH_3CHBr$ | $CH_3$ | H | $C_2H_5$ | H | H | H | S | 1.4327 |
| 146 | $CH_2BrCH_2$ | $CH_3$ | H | $C_2H_5$ | H | H | H | S | 1.4293 |
| 147 | $CH_2Cl$ | $CH_3$ | H | $C_2H_5$ | H | H | H | S | 1.5279 |
| 148 | $CHCl_2$ | $CH_3$ | $CH_3$ | H | H | H | $n$-$C_3H_7$ | H | O | 1.4604 |

TABLE I-continued

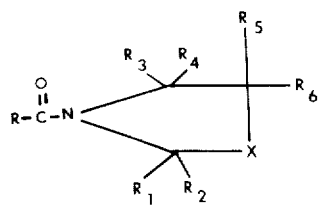

| COMPOUND NUMBER | R | $R_1$ | $R_2$ | $R_3$ | $R_4$ | $R_5$ | $R_6$ | X | m.p. °C. or $n_D^{30}$ |
|---|---|---|---|---|---|---|---|---|---|
| 149 | $CH_2Cl$ | $CH_3$ | $CH_3$ | H | H | n-$C_3H_7$ | H | O | 1.4532 |

It is clear that the classes of herbicidal agents described and illustrated herein are characterized as effective herbicides exhibiting such activity. The degree of this herbicidal activity varies among specific compounds and among combinations of specific compounds within the classes. Similarly, the degree of activity to some extent varies among the species of plants to which a specific herbicidal compound or combination may be applied. Thus, selection of a specific herbicidal compound or combination to control undesirable plant species readily may be made. Within the present invention are prevention of injury to a desired crop species in the presence of a specific compound or combination may be achieved. The beneficial plant species which can be protected by this method is not intended to be limited by the specific crops employed in the examples.

The herbicidal compounds employed in the utility of this invention are active herbicides of a general type. That is, the members of the classes are herbicidally effective against a wide range of plant species with no discrimination between desirable and undesirable species. The method of controlling vegetation comprises applying an herbicidally effective amount of the herein-described herbicidal compounds to the area or plant locus where control is desired.

An herbicide as used herein means a compound which controls or modifies the growth of vegetation or plants. Such controlling or modifying effects include all deviations from natural development; for example, killing, retardation, defoliation, desiccation, regulation, stunting, tillering, stimulation, dwarfing and the like. By "plants" it is meant germinant seeds, emerging seedlings, and established vegetation, including the roots and above-ground portions.

The compounds of this invention were employed in effective herbicidal antidote compositions comprising thiocarbamates in combination with antidote compounds described hereinabove. They were tested in the following manner.

Corn Seed Treatment Test

Small flats were filled with Felton loamy sand soil. Soil incorporated herbicides were applied at this time. The soil from each flat was placed into a five-gallon cement mixer where the soil was mixed as the herbicides were applied using a predetermined amount of a stock solution containing 936 mg. of 75.5% active ingredient to 100 ml. of water. One ml. of stock solution was applied to the soil in a volumetric pipet for each pound of herbicide desired. One ml. of stock solution contained 7 mg. of herbicide which equals 1 pound per acre when applied to the soil in the flats. After the herbicide incorporation, the soil was placed back into the flats.

Flats of herbicide-treated and untreated soil were then ready to be planted. A pint sample of soil was removed from each flat and placed next to each flat for later use in covering up the seeds. The soil was leveled and rows one-half inch deep were made for planting seeds. Alternating rows of treated and untreated crop seeds were sown. In each test, six PAG 344T field corn seeds were planted in each row. Rows were approximately 1½ inches apart in the flat. Seeds were treated by either (1) placing 50 mg. of the antidote compound with 16 grams of corn seed in a suitable container and shaking them until the seeds were uniformly covered with the compound; or (2) preparing a stock solution by dissolving 50 mg. of the antidote compound in 5 ml. of acetone then using 0.5 ml. of the solution to treat 10 g. of corn seed (0.05% w/w). Antidote compounds were also applied as liquid slurries and powders or dusts. In some cases, acetone was used to dissolve powdered or solid compounds so they could be more effectively applied to the seeds.

After the flats were seeded, they were covered with the one pint of soil which had been removed just prior to planting. Flats were placed on greenhouse benches where temperatures ranged from 70°–90°F. Flats were watered by sprinkling as needed to assure good plant growth. Per cent control ratings were taken 2, 3 and 4 weeks after the treatments were applied.

In each test, the herbicide was applied alone, in combination with the seed protectant, and the seed protectant was applied alone to check for phytotoxicity. The untreated adjacent row was employed to observe any beneficial lateral movement of the antidote compound through the soil. The degree of the effect was noted by comparison with the control. The results of these tests were tabulated in Table II.

TABLE II

Per Cent Injury to Corn from EPTC*
Seed Treatment Test

| COMPOUND NUMBER | Per Cent Injury, 2 weeks | |
|---|---|---|
| | Treated Seed (0.05% w/w) | Untreated Seed Adjacent Row |
| 1** | 5 | 30 |
| 2 | 70 | 80 |
| 3** | 40 | 60 |

TABLE II-continued

Per Cent Injury to Corn from EPTC*
Seed Treatment Test

| COMPOUND NUMBER | Per Cent Injury, 2 weeks Treated Seed (0.05% w/w) | Untreated Seed Adjacent Row |
|---|---|---|
| 4 | 10 | 50 |
| 5 | 30 | 60 |
| 6 | 0 | 0 |
| 7 | 40 | 55 |
| 8 | 0 | 15 |
| 9 | 10 | 55 |
| 10 | 20 | 60 |
| 11 | 30 | 50 |
| 12 | 10 | 40 |
| 13 | 50 | 70 |
| 14 | 0 | 20 |
| 15 | 20 | 50 |
| 16 | 10 | 55 |
| 17 | 30 | 50 |
| 18 | 20 | 50 |
| 19 | 40 | 50 |
| 20 | 20 | 60 |
| 21 | 50 | 50 |
| 22 | 60 | 60 |
| 23 | 50 | 60 |
| 24 | 20 | 60 |
| 25 | 20 | 70 |
| 26 | 20 | 60 |
| 27 | 20 | 60 |
| 28 | 60 | 70 |
| 29 | 0 | 5 |
| 30 | 20 | 5 |
| EPTC 6E Untreated Seed | — | 70 |
| | | 80 (4 wk.) ** |

*=S-ethyl dipropylthiocarbamate 6E: 6 lb./A preplant incorporated
**=Seed treatment 0.01% w/w With 2-chloro-2′,6′-diethyl-N-(methoxymethyl-)acetanilide at 2 lb/A. as a seed treatment (0.5%), Compound No. 144 gave 100% protection to sorghum (Milo).

Procedure: Multicrop Antidote Screen

Plastic flats were filled with Felton loamy sand soil. Since a variety of grass and broadleaf crops were used in these tests, EPTAM (EPTC) was incorporated at ½ and 5 lb/A, while a constant rate of 5 lb/A of the additive was used. EPTAM (EPTC) and the herbicide additive were applied separately by pipetting measured amounts of the appropriate stock solutions into the soil during incorporation in a 5 gallon rotary cement mixer. Stock solutions for EPTAM were prepared as follows:
A. ½ lb/A: 670 mg. of EPTC 6E (75.5% a.i.) was diluted with 500 ml. of deionized water so that 2 ml. equals ½ lb/A/plastic flat.
B. 5 lb/A: 6700 mg. of EPTC 6E (75.5%) was diluted with 500 ml. of deionized water so that 2 ml. equals 5 lb/A/plastic flat.

Additive stock solutions were prepared by diluting 102 mg. of technical material with 10 ml. of acetone 1% Tween 20 (polyoxy-ethylene sorbitan monolaurate) so that 2 ml. equals 5 lb/A/flat.

After the soil was treated with both herbicide and additive the soil was transferred from the mixer back into the flat where it was then prepared for seeding. The initial step in preparation was to remove a 1 pint sample of soil from each flat to be retained and used to cover the seeds after planting. The soil was then leveled and rows ¼ inch deep were made in each flat. Flats treated with 5 lb/A of EPTAM were seeded to DeKalb XL-44 corn (*Zea maize*), US H9 sugarbeets (*Beta vulgare*), small seeded gray striped sunflower (*Helianthus annus*), Acala cotton (*Gossypium hirsutum*), Brag soybeans (*Glycine max*) and oilseed rape (*Brassica napus*). Flats treated with ½ lb/A of EPTAM were seeded to red oats (*Avena byzantina*), R-10 [sorghum] (*Sorgum vulgare*), Fremont HRS wheat (*Triticum aestivum*), giant foxtail (*Seteria feberii*), Calrose rice (*Oryza sativa*) and Blue Mariate barley (*Hordeum vulgare*). Seeds were then covered with the pint soil sample removed prior to seeding.

The flats were then placed on greenhouse benches where temperatures were maintained between 70°–90°F. The soil was watered by sprinkling to assure good plant growth.

Injury ratings were taken 2 and 4 weeks after the treatments were applied. Soil treated with EPTAM alone at ½ or 5 lb/A was included to provide a basis for determining the amount of injury reduction provided by the herbicide antidotes. The per cent protection of various representative crops is reported in Table III. The per cent protection is determined by a comparison with flats not treated with the candidate antidote.

TABLE III

Multicrop Screen Results
Per Cent Protection

| COMPOUND NUMBER | Rate of EPTC lb/A | Crop | % Protection (2 weeks) |
|---|---|---|---|
| 31 | 0.5 | barley | 56 |
|    |     | rice | 30 |
| 32 | 0.5 | barley | 56 |
|    |     | rice | 30 |
|    |     | corn | 100 |
| 33 | 0.5 | rice | 30 |
|    |     | barley | 44 |
| 34 | 0.5 | barley | 88 |
|    | 5.0 | corn | 100 |
| 35 | 0.5 | barley | 44 |
|    | 5.0 | corn | 100 |
| 36 | 5.0 | corn | 100 |
| 37 | 5.0 | corn | 100 |
| 38 | 0.5 | barley | 88 |
|    | 5.0 | corn | 100 |
|    | 5.0 | sunflower | 50 |
| 39 | 5.0 | corn | 100 |
|    | 5.0 | sunflower | 25 |
|    | 5.0 | oilseed rape | 60 |
| 40 | 5.0 | corn | 100 |
|    | 5.0 | sunflower | 25 |
| 41 | 0.5 | barley | 50 |
|    | 5.0 | corn | 100 (4 weeks) |
| 42 | 5.0 | corn | 56 (4 weeks) |
| 43 | 5.0 | corn | 93 (4 weeks) |
| 44 | 5.0 | corn | 28 (4 weeks) |
| 45 | 0.5 | barley | 50 |
|    | 5.0 | sunflower | 81 |
| 46 | 0.5 | rice | 100 (4 weeks) |
| 47 | 0.5 | rice | 100 (4 weeks) |
|    | 0.5 | barley | 75 (4 weeks) |
|    | 5.0 | oilseed rape | 68 (4 weeks) |
| 48 | 0.5 | barley | 25 |
|    | 5.0 | sunflower | 67 (4 weeks) |
| 49 | 0.5 | sorghum | 50 |
|    | 0.5 | barley | 50 |
|    | 5.0 | corn | 100 (4 weeks) |
| 50 | 5.0 | corn | 10 (4 weeks) |
| 51 | 5.0 | corn | 42 (4 weeks) |
| 52 | 5.0 | corn | 100 (4 weeks) |
| 53 | 0.5 | rice | 100 (4 weeks) |
|    | 0.5 | barley | 50 (4 weeks) |
|    | 5.0 | corn | 70 (4 weeks) |
| 54 | 0.5 | barley | 50 |
|    | 5.0 | corn | 100 (4 weeks) |
| 55 | 0.5 | wheat | 20 (4 weeks) |
|    | 0.5 | barley | 100 (4 weeks) |
|    | 5.0 | corn | 93 (4 weeks) |
| 56 | 0.5 | sorghum | 10 (4 weeks) |
| 57 | 0.5 | barley | 50 |
|    | 5.0 | corn | 100 (4 weeks) |
| 58 | 0.5 | rice | 100 (4 weeks) |
| 59 | 5.0 | corn | 93 (4 weeks) |
| 60 | 0.5 | rice | 100 (4 weeks) |
|    | 5.0 | corn | 42 (4 weeks) |
| 61 | 0.5 | sorghum | 40 (4 weeks) |
|    | 0.5 | barley | 75 (4 weeks) |

TABLE III-continued

Multicrop Screen Results
Per Cent Protection

| COMPOUND NUMBER | Rate of EPTC lb/A | Crop | % Protection (2 weeks) |
|---|---|---|---|
| | 5.0 | rice | 70 (4 weeks) |
| 62 | 5.0 | oilseed rape | 65 (4 weeks) |
| 63 | 0.5 | barley | 75 |
| 64 | 5.0 | corn | 42 (4 weeks) |
| 65 | 5.0 | corn | 70 (4 weeks) |
| 66 | 5.0 | corn | 100 (4 weeks) |
| 67 | 5.0 | corn | 28 (4 weeks) |
| 68 | 0.5 | rice | 100 (4 weeks) |
| | 5.0 | corn | 93 (4 weeks) |
| 69 | 5.0 | corn | 42 (4 weeks) |
| 70 | 5.0 | corn | 100 (4 weeks) |
| 71 | 5.0 | corn | 70 (4 weeks) |
| 72 | 0.5 | rice | 100 (4 weeks) |
| | 0.5 | barley | 50 (4 weeks) |
| | 5.0 | corn | 100 (4 weeks) |
| 73 | 5.0 | corn | 100 (4 weeks) |
| 74 | 5.0 | corn | 42 (4 weeks) |
| 75 | 0.5 | sorghum | 71 |
| | 0.5 | wheat | 60 |
| | 5.0 | corn | 87 |
| | 5.0 | oilseed rape | 71 |
| 76 | 5.0 | corn | 56 (4 weeks) |
| 77 | 5.0 | corn | 100 (4 weeks) |
| | 5.0 | sugarbeets | 28 (4 weeks) |
| 78 | 0.5 | rice | 100 (4 weeks) |
| | 5.0 | corn | 100 (4 weeks) |
| | 5.0 | sunflower | 81 (4 weeks) |
| 79 | 0.5 | barley | 50 |
| | 5.0 | corn | 100 (4 weeks) |
| | 5.0 | sunflower | 67 (4 weeks) |
| 80 | 5.0 | corn | 70 (4 weeks) |
| | 5.0 | oilseed rape | 56 (4 weeks) |
| 81 | 0.5 | barley | 50 (4 weeks) |
| | 5.0 | sunflower | 67 (4 weeks) |
| 82 | 5.0 | corn | 56 (4 weeks) |
| 83 | 0.5 | rice | 100 (4 weeks) |
| 84 | 0.5 | rice | 100 (4 weeks) |
| | 0.5 | barley | 50 (4 weeks) |
| 85 | 0.5 | rice | 100 (4 weeks) |
| | 0.5 | barley | 75 (4 weeks) |
| | 5.0 | corn | 93 (4 weeks) |
| 86 | 0.5 | barley | 50 (4 weeks) |
| | 5.0 | corn | 100 (4 weeks) |
| 87 | 5.0 | corn | 93 (4 weeks) |
| 88 | 0.5 | barley | 45 |
| 89 | 0.5 | wheat | 67 |
| | 5.0 | oilseed rape | 75 |
| 90 | 0.5 | wheat | 15 |
| 91 | 0.5 | sorghum | 50 |
| | 5.0 | corn | 84 |
| 92 | 5.0 | oilseed rape | 75 |
| 93 | 5.0 | oilseed rape | 75 |
| 94 | 5.0 | oilseed rape | 75 |
| 95 | 5.0 | oilseed rape | 75 |
| 96 | 5.0 | corn | 80 |
| 97 | 0.5 | barley | 50 |
| 98 | 5.0 | sunflower | 60 |
| 99 | 0.5 | barley | 88 |
| 100 | 5.0 | corn | 100 |
| 101 | 5.0 | sunflower | 100 |
| 102 | 5.0 | oilseed rape | 50 |
| 103 | 0.5 | sorghum | 30 (4 weeks) |
| | 5.0 | corn | 100 |
| 104 | 0.5 | rice | 30 (4 weeks) |
| | 0.5 | sorghum | 30 (4 weeks) |
| 105 | 0.5 | wheat | 30 (4 weeks) |
| | 0.5 | barley | 75 (4 weeks) |
| 106 | 5.0 | sunflower | 20 (4 weeks) |
| 107 | 0.5 | wheat | 40 (4 weeks) |
| | 0.5 | barley | 60 (4 weeks) |
| | 5.0 | corn | 100 (4 weeks) |
| 108 | 5.0 | oilseed rape | 75 |
| 109 | 5.0 | oilseed rape | 75 |
| 110 | 5.0 | oilseed rape | 75 |
| 111 | 5.0 | sunflower | 60 |
| 112 | 5.0 | oilseed rape | 75 |
| 113 | 5.0 | oilseed rape | 67 |
| 114 | 5.0 | oilseed rape | 33 |
| 115 | 0.5 | barley | 70 (4 weeks) |
| | 5.0 | corn | 10 (4 weeks) |
| 116 | 0.5 | barley | 58 (4 weeks) |
| | 5.0 | sunflower | 60 (4 weeks) |
| | 5.0 | corn | 100 (4 weeks) |
| 117 | 0.5 | barley | 58 (4 weeks) |
| | 5.0 | corn | 100 (4 weeks) |
| 118 | 0.5 | barley | 58 (4 weeks) |
| | 5.0 | corn | 65 (4 weeks) |
| 119 | 0.5 | barley | 68 (4 weeks) |
| | 5.0 | corn | 100 (4 weeks) |
| 120 | 5.0 | sunflower | 30 |
| 121 | 0.5 | rice | 67 (4 weeks) |
| | 5.0 | oilseed rape | 60 (4 weeks) |
| 122 | 0.5 | barley | 58 (4 weeks) |
| | 5.0 | corn | 100 (4 weeks) |
| 123 | 0.5 | rice | 44 (4 weeks) |
| 124 | 0.5 | rice | 67 (4 weeks) |
| | 0.5 | barley | 58 (4 weeks) |
| 125 | 0.5 | rice | 88 (4 weeks) |
| 126 | 0.5 | rice | 100 |
| | 0.5 | barley | 100 |
| 127 | 0.5 | rice | 78 |
| | 0.5 | barley | 64 |
| 128 | 0.5 | rice | 78 |
| | 0.5 | barley | 57 |
| | 5.0 | oilseed rape | 60 |
| 129 | 0.5 | rice | 78 |
| | 0.5 | barley | 43 |
| | 5.0 | sunflower | 100 |
| 130 | 0.5 | rice | 100 |
| | 0.5 | barley | 43 |
| | 5.0 | oilseed rape | 40 |
| | 5.0 | soybeans | 33 |
| 131 | 0.5 | barley | 43 |
| | 5.0 | sunflower | 100 |
| | 5.0 | oilseed rape | 80 |
| | 5.0 | soybeans | 47 |
| 132 | 0.5 | rice | 78 |
| | 0.5 | oats | 50 |
| | 0.5 | barley | 57 |
| | 5.0 | oilseed rape | 100 |
| | 5.0 | corn | 58 |
| 133 | 0.5 | barley | 57 |
| | 0.5 | oats | 40 |
| | 5.0 | sugarbeets | 45 |
| | 5.0 | oilseed rape | 100 |
| 134 | 0.5 | barley | 43 |
| | 5.0 | soybeans | 33 |
| | 5.0 | oilseed rape | 80 |
| 135 | 0.5 | oats | 60 |
| | 5.0 | corn | 100 |
| | 5.0 | oilseed rape | 100 |
| 136 | 0.5 | rice | 55 |
| | 0.5 | barley | 57 |
| | 5.0 | corn | 100 |
| | 5.0 | oilseed rape | 80 |
| 137 | 0.5 | barley | 43 |
| | 5.0 | sunflower | 70 |
| | 5.0 | soybeans | 33 |
| 138 | 0.5 | rice | 78 |
| | 0.5 | barley | 71 |
| | 5.0 | oilseed rape | 60 |
| 139 | 5.0 | sunflower | 70 |
| | 5.0 | oilseed rape | 60 |
| 140 | 5.0 | sunflower | 100 |
| | 5.0 | oilseed rape | 60 |
| | 5.0 | soybeans | 33 |
| 141 | 5.0 | soybeans | 47 |
| | 5.0 | oilseed rape | 60 |
| 142 | 0.5 | rice | 86 |
| | 0.5 | barley | 62.5 |
| 143 | 0.5 | rice | 100 |
| | 0.5 | barley | 87.5 |
| 144 | 0.5 | sorghum | 100 |
| | 0.5 | rice | 86 |
| | 0.5 | barley | 100 |
| | 5.0 | corn | 100 |
| 145 | 0.5 | rice | 100 |
| | 0.5 | barley | 100 |
| 146 | 0.5 | barley | 75 |
| | 5.0 | oilseed rape | 100 |
| 147 | 0.5 | rice | 72 |
| | 5.0 | corn | 88 |
| 148* | 1.0 | sorghum | 80 (4 weeks) |
| | 5.0 | corn | 100 (4 weeks) |
| 149* | 5.0 | corn | 100 (4 weeks) |

*Herbicide used VERNAM (S-propyl N,N-dipropylthiocarbamate).

In-furrow method of application employed to apply antidote compound. Stock solutions used:

1 lb/A: 633 mg. of VERNAM (75% a.i.) was diluted with 500 ml. of deionized water so that 4 ml. applied is equivalent to 1 lb/A per flat.

5 lb/A: 633 mg. of VERNAM (75% a.i.) was diluted with 100 ml. of deionized water so that 4 ml. is equivalent to 5 lb/A per flat.

When used with 2-chloro-2',6'-diethyl-N-(methoxymethyl) acetanilide at 2 lb/A, Compounds No. 1 and 30 at 5 lb/A after 4 weeks gave 100 per cent protection to sorghum. Compound No. 1 also gave 67 per cent protection to wheat.

When used with 3-(3,4-dichlorophenyl)-1,1-dimethylurea at 1 lb/A, Compounds No. 1 and 30 at 5 lb/A each gave 60 per cent protection to cotton; Compound No. 1 also gave 60 per cent protection to corn; and Compound No. 30 gave 43 per cent protection to corn.

The antidote compounds and compositions of the present invention can be used in any convenient form. Thus, the antidote compounds can be formulated into emulsifiable liquids, emulsifiable concentrates, liquid, wettable powder, powders, granular or any other convenient form. In its preferred form, a non-phytotoxic quantity of an herbicidal antidote compound is admixed with a selected herbicide and incorporated into the soil prior to or after planting the seed. It is to be understood, however, that the herbicides can be incorporated into the soil and thereafter the antidote compound can be incorporated into the soil. Moreover, the crop seed itself can be treated with a non-phytotoxic quantity of the compound and planted into the soil which has been treated with herbicides, or untreated with the herbicide and subsequently treated with the herbicide. The addition of the antidote compound does not effect the herbicidal activity of the herbicides.

The amount of antidote compound present can range between about 0.001 to about 30 parts by weight of antidote compound described herein per each part by weight of herbicide. The exact amount of antidote compound will usually be determined on economic ratios for the most effective amount usable. It is understood that a non-phytotoxic quantity of antidote compound will be employed in the herbicidal compositions described herein.

What is claimed:

1. A compound having the formula

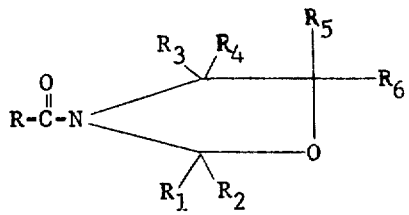

in which R is selected from the group tribromomethyl, monochloromethyl, dichloromethyl, 1-bromoethyl, monobromomethyl, 1,2-dibromoethyl, 2-chloropropyl, 1-bromopropyl, 1-bromobutyl, 3-chloropropyl, 5-bromopentyl; $R_1$ is methyl; $R_2$ is methyl; $R_5$ is methyl; and $R_3$, $R_4$ and $R_6$ are each hydrogen.

2. A compound according to claim 1 in which R is tribromomethyl.

3. A compound according to claim 1 in which R is monochloromethyl.

4. A compound according to claim 1 in which R is 1-bromoethyl.

5. A compound according to claim 1 in which R is monobromomethyl.

6. A compound according to claim 1 in which R is 1,2-dibromoethyl.

7. A compound according to claim 1 in which R is 2-chloropropyl.

8. A compound according to claim 1 in which R is 1-bromopropyl.

9. A compound according to claim 1 in which R is 1-bromobutyl.

10. A compound according to claim 1 in which R is 3-chloropropyl.

11. A compound according to claim 1 in which R is 5-bromopentyl.

12. The compound having the formula

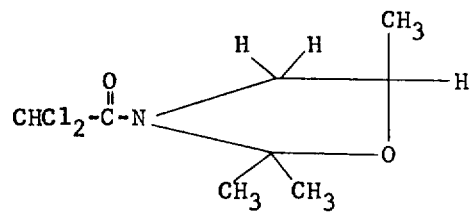

13. The compound having the formula

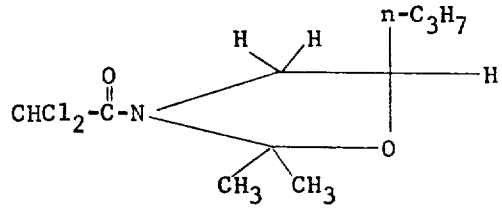

* * * * *